(12) United States Patent
Brady et al.

(10) Patent No.: US 8,841,904 B1
(45) Date of Patent: Sep. 23, 2014

(54) NONDESTRUCTIVE INSPECTION PROBE AND METHOD

(75) Inventors: Steven K. Brady, Renton, WA (US); Donald D. Palmer, Jr., Ballwin, MO (US); Jeffrey R. Kollgaard, Seattle, WA (US)

(73) Assignee: The Boeing Company, Chicago, IL (US)

( * ) Notice: Subject to any disclaimer, the term of this patent is extended or adjusted under 35 U.S.C. 154(b) by 407 days.

(21) Appl. No.: 13/029,329

(22) Filed: Feb. 17, 2011

(51) Int. Cl.
*G01N 27/82* (2006.01)
*G01N 27/90* (2006.01)
*G01N 27/72* (2006.01)
*G01R 33/09* (2006.01)

(52) U.S. Cl.
USPC ........... 324/242; 324/238; 324/239; 324/240; 324/252

(58) Field of Classification Search
USPC .......................................... 324/239, 238, 242
See application file for complete search history.

(56) References Cited

U.S. PATENT DOCUMENTS

| | | | | |
|---|---|---|---|---|
| 4,271,393 A * | 6/1981 | Hansen et al. | ................ | 324/240 |
| 6,150,809 A * | 11/2000 | Tiernan et al. | ................ | 324/238 |
| 7,115,869 B2 | 10/2006 | Shelley et al. | | |
| 2003/0080735 A1 * | 5/2003 | Wache | ........... | 324/235 |
| 2003/0173959 A1 * | 9/2003 | Paulson et al. | ................ | 324/220 |
| 2004/0245997 A1 * | 12/2004 | Plotnikov et al. | ............. | 324/529 |
| 2006/0290349 A1 * | 12/2006 | Na et al. | ........................ | 324/228 |
| 2009/0206831 A1 * | 8/2009 | Fermon et al. | ................ | 324/240 |

FOREIGN PATENT DOCUMENTS

GB 2273782 A * 6/1994

* cited by examiner

*Primary Examiner* — Bot Ledynh
(74) *Attorney, Agent, or Firm* — Hanley, Flight & Zimmerman, LLC

(57) ABSTRACT

A probe for detecting distortions in a material includes a probe body, a ferrite core in the probe body, an excitation coil encircling the ferrite core and adapted to generate eddy currents, further magnetic shielding surrounding the excitation coil, and at least one giant magnetoresistive (GMR) sensor disposed in magnetic field-communicating relationship with the excitation coil and off-center with respect to the excitation coil's axis.

19 Claims, 6 Drawing Sheets

NONDESTRUCTIVE INSPECTION PROBE AND METHOD

TECHNICAL FIELD

The disclosure generally relates to nondestructive methods of inspecting structures for the presence of distortions or flaws in the structures. More particularly, the disclosure relates to a nondestructive inspection (NDI) probe and method which utilize giant magnetoresistance (GMR)-based sensors to detect the presence of distortions or flaws in a thick or multi-layer structure.

BACKGROUND

In aircraft and other structures in which two or more metal, composite or other materials are joined by fasteners, stress may induce distortions in the materials. It may be necessary or desirable to detect, assess and repair the distortions prior to continued service of the aircraft or other structure. Eddy currents induced in a material may be perturbed by the presence of distortions in the material. Therefore, distortions in a material may be detected and assessed by analyzing changes in a magnetic field created by the eddy currents in the material. Conventional probes may detect the magnetic fields created by eddy currents using inductive coils. However, the minimum detectable distortion dimensions using these conventional inductive probes may be undesirably large for some applications.

Giant magnetoresistance (GMR) sensors are sensitive to magnetic fields over a broad range of frequencies all the way down to 0 Hz. The sensitivity of an inductive coil is reduced as the frequency of the magnetic field which is measured by the inductive coil decreases. Inspection of distortions within or through thick, electrically conductive parts may require low-frequency magnetic fields due to the skin depth phenomenon in conductors.

Therefore, a nondestructive inspection (NDI) probe and method which utilize giant magnetoresistance (GMR)-based sensors to detect changes in a magnetic field which is created by eddy currents in an electrically-conductive material, with the capability to detect and assess the magnitude of distortions or flaws having a relatively small size in the material are needed.

SUMMARY

The disclosure is generally directed to a probe for detecting distortions or flaws in a material. An illustrative embodiment of the probe includes a probe body of generally cylindrical geometry housing an inner shield made of a ferromagnetic material of low electrical conductivity (e.g. ferrite), an excitation coil encircling the inner shield and adapted to generate eddy currents, at least one giant magnetoresistive (GMR) sensor disposed in magnetic field-communicating relationship with the excitation coil and off-center with respect to the axis of the excitation coil, and an outer shield made of a similar material to the inner shield.

In some embodiments, the probe for detecting distortions in a material may include a probe body having a generally elongated, cylindrical probe body wall with a probe body interior; a ferrite core having an interior core surface in the probe body interior of the probe body; an excitation coil encircling the ferrite core and adapted to generate eddy currents; and a plurality of giant magnetoresistive (GMR) sensors disposed in magnetic field-communicating relationship with the excitation coil and off-center with respect to the excitation coil.

The disclosure is further generally directed to a method for detecting distortions in a material. An illustrative embodiment of the method includes exciting at least one giant magnetoresistive (GMR) sensor; generating a sine wave at a predetermined inspection amplitude and frequency; inducing a magnetic field in an eddy current excitation coil by communicating the sine wave to the eddy current excitation coil; inducing eddy currents in an inspection surface by placing the eddy current excitation coil in close proximity with the inspection surface; measuring a magnetic flux of the magnetic field induced by the eddy currents; detecting and measuring voltage changes corresponding to the magnetic flux; and analyzing the voltage changes for characteristics indicative of a distortion in the material.

BRIEF DESCRIPTION OF THE ILLUSTRATIONS

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the claims. Furthermore, there is no intention to be bound by any expressed or implied theory presented in the preceding technical field, background, brief summary or the following detailed description.

Figure 1:
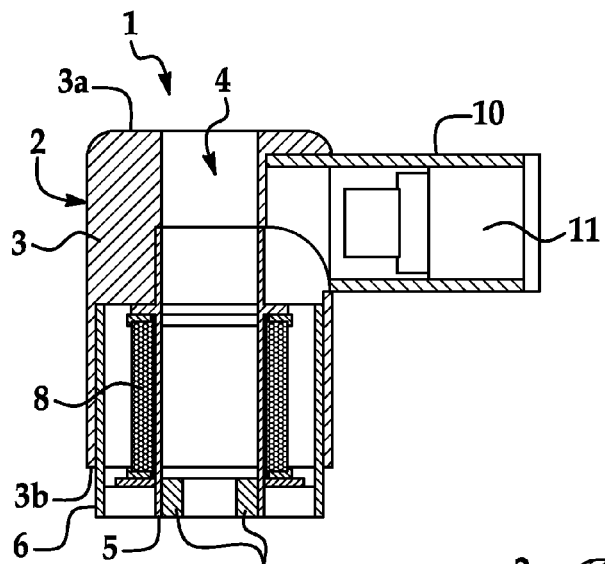
FIG. 1 is a sectional view of an illustrative embodiment of a nondestructive inspection (NDI) probe which utilizes giant magnetoresistance (GMR)-based sensors.
Figure 2:
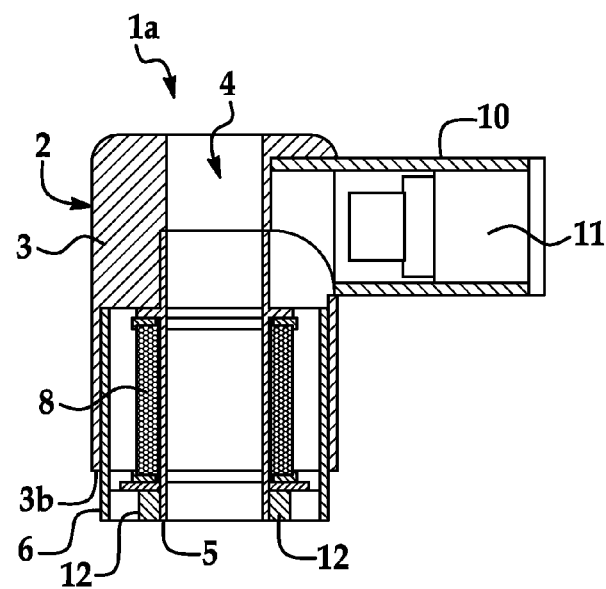
FIG. 2 is a sectional view of an alternative illustrative embodiment of an NDI probe which utilizes giant magnetoresistance (GMR)-based sensors.
Figure 3:
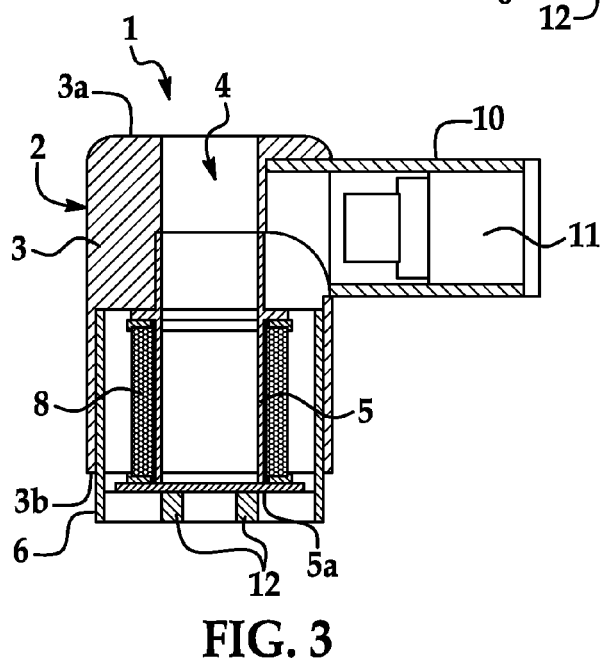
FIG. 3 is a sectional view of another alternative illustrative embodiment of an NDI probe which utilizes giant magnetoresistance (GMR)-based sensors.

Referring initially to FIGS. 1-3, an illustrative embodiment of the NDI (nondestructive inspection) probe is generally indicated by reference numeral 1 in FIG. 1. The NDI probe 1 may include a probe body 2 having a probe body wall 3 with a first wall end 3a and a second wall end 3b. The probe body wall 3 may have a generally elongated, cylindrical configuration and may form a probe body interior 4. A generally cylindrical inner shield 5 may extend from the probe body wall 3 through the probe body interior 4. A generally cylindrical outer shield 6 may extend from the probe body wall 3 outside and in generally concentric and spaced-apart relationship with respect to the inner shield 5. The inner shield 5 and the outer shield 6 may extend beyond the second wall end 3b of the probe body wall 3.

An eddy current excitation coil 8 may be wound around the inner shield 5 between the inner shield 5 and the outer shield 6. The eddy current excitation coil 8 may be enameled wire (magnet wire) which forms a solenoid when wound around the inner shield 5. Several turns of the eddy current excitation coil 8 may form the solenoid around the inner shield 5. The multiple turns of the solenoid may cause the impedance of the solenoid to fall in the ones to hundreds of Ohms range at the intended excitation frequency of the eddy current excitation coil 8. The multiple turns of the solenoid may also generate an excitation magnetic field when a sine-wave current flows through the eddy current excitation coil 8, as will be hereinafter described.

At least one giant magnetoresistive (GMR) sensor 12 may be disposed in magnetic field-communicating relationship with respect to the eddy current excitation coil 8. The GMR sensor or sensors 12 may be off-center with respect to the axis of the eddy current excitation coil 8. In some embodiments of the NDI probe 1, at least one GMR sensor 12 may be provided on the interior surface of the inner shield 5. In some embodiments, multiple GMR sensors 12 may be spaced around the circumference of the interior surface of the inner shield 5. For example and without limitation, in some embodiments, four GMR sensors 12 may be arranged in generally 90-degree relationship with respect to each other around the interior circumference of the inner shield 5.

As shown in FIG. 2, in some embodiments of the NDI probe 1a, at least one GMR sensor 12 may be provided between the inner shield 5 and the outer shield 6, such as on the exterior surface of the inner shield 5, for example and without limitation. In some embodiments of the NDI probe 1a, multiple GMR sensors 12 may be spaced around the circumference between the inner shield 5 and the outer shield 6. As shown in FIG. 3, in some embodiments of the NDI probe 1b, the inner shield 5 may terminate short of the outer shield 6. At least one GMR sensor 12 may be provided at the lower edge 5a of the inner shield 5. In some embodiments of the NDI probe 1b, multiple GMR sensors 12 may be spaced around the circumference of the lower edge 5a of the inner shield 5.

Figure 4:
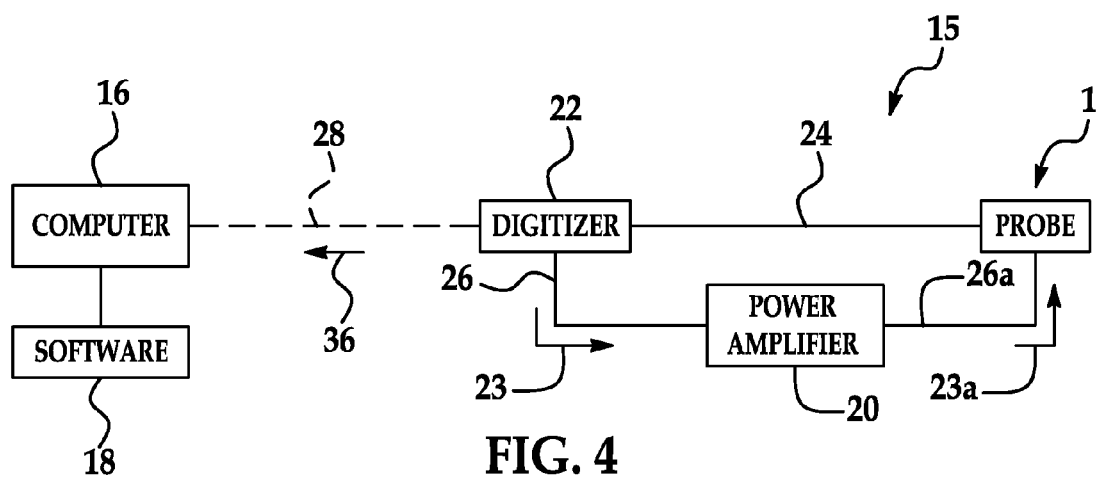
FIG. 4 is a block diagram of an exemplary NDI system in implementation of an illustrative embodiment of the NDI probe.

Referring next to FIG. 4, an NDI system 15 which utilizes an illustrative embodiment of the NDI probe 1 is shown. The NDI system 15 may include a computer 16 with supporting software 18. A digitizer 22 (also known as an A-to-D and D-to-A device) may interface with the probe 1 through a probe cable 24. Sensor wiring 13 (FIG. 2) may connect the individual GMR sensor 12 in the NDI probe 1 to the digitizer 22 through the probe cable 24. A power amplifier 20 may interface with the digitizer 22 through a coil drive signal cable 26. The power amplifier 20 may interface with the probe 1 through a coil drive cable 26a. The computer 16 and the digitizer 22 may interface with each other through a communication pathway 28. In some embodiments, the communication pathway 28 may include wireless transmission signals. In some embodiments, the communication pathway 28 may include a transmission cable.

Figure 5:
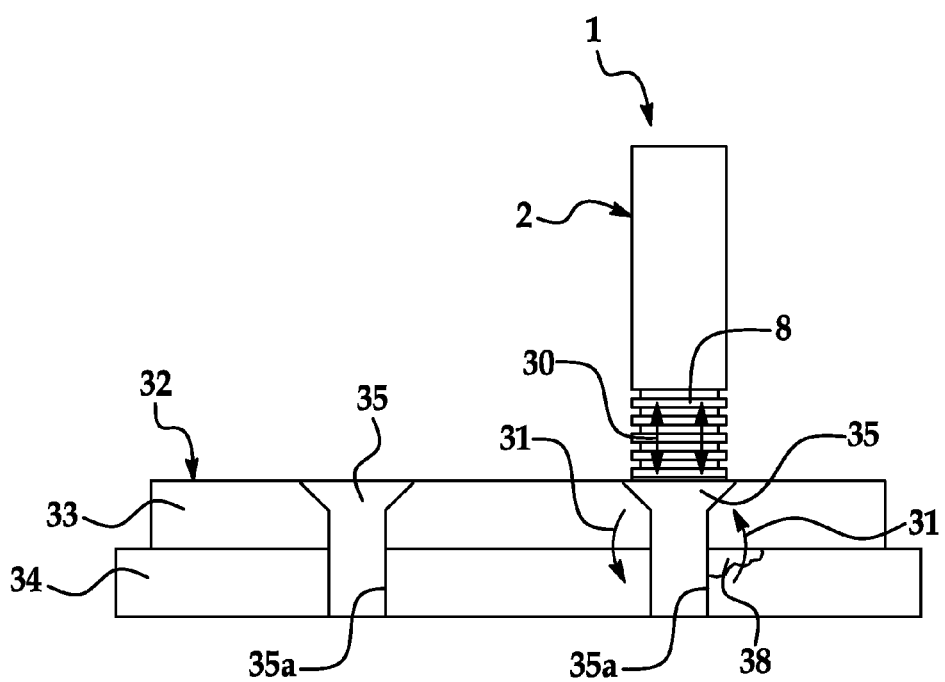
FIG. 5 is a sectional view of a multi-layered structure, with an illustrative embodiment of the NDI probe applied against a fastener securing adjacent layers of the structure to detect a distortion in one of the layers adjacent to the fastener.
Figure 6:
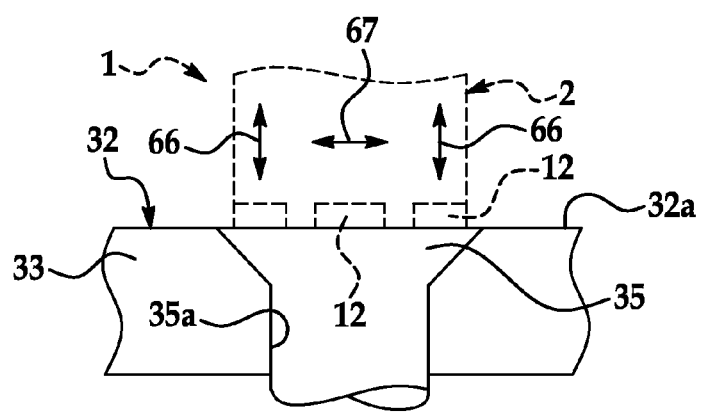
FIG. 6 is a diagram which illustrates orientation of the sensitive axes of respective GMR sensors of the NDI probe with respect to a surface under inspection.

Referring next to FIGS. 5 and 6, in exemplary application, the NDI probe 1 is adapted to detect the presence of a distortion 38 (FIG. 6) such as a crack, for example and without limitation, in a structure 32 in which the presence of a distortion 38 may be suspected. The structure 32 may include a first structural member 33 and a second structural member 34. Multiple fasteners 35 may extend into respective fastener openings 35a and secure the first structural member 33 to the second structural member 34 in the structure 32. The first structural member 33 and the second structural member 34 may be metal or composite, for example and without limitation. The distortion 38 may be located in the first structural member 33 or the second structural member 34 (as shown) adjacent to a fastener 35.

After calibration of the NDI probe 1, which will be hereinafter described, the structure 32 may be inspected for the presence of a distortion 38 as follows. Through the communication pathway 28, the software 18 on the computer 16 may excite the GMR sensors 12 on the probe 1 with a DC voltage. The software 18 may also command the digitizer 22 to generate a sine-wave signal 23 at the desired inspection frequency (typically chosen from 50 to a few thousand Hz). The digitizer 22 may feed the sine-wave signal 23 into the power amplifier 20, which may form an amplified sine-wave signal 23a. The amplified sine-wave signal 23a may be transmitted to the NDI probe 1, where the amplified sine-wave signal 23a may flow through the eddy current excitation coil 8 of the probe 1 and form a magnetic field 30 (FIG. 6).

As shown in FIG. 6, the NDI probe 1 may be placed against each fastener 35 which secures the first structural member 33 to the second structural member 34. Upon placement of the NDI probe 1 against the typically metal fastener 35, the magnetic field 30 may cause eddy currents 31 to flow in the fastener 35, first structural member 33, and second structural member 34, generally beneath the windings of the eddy current excitation coil 8. Distortions 39 in the structure 32 may interrupt the flow of the eddy currents 31 and perturb or form magnetic flux in the magnetic field 30 in the vicinity of the NDI probe 1.

The GMR sensor or sensors 12 on the probe 1 may measure the perturbed magnetic field 30. The perturbations in the magnetic field 30 may cause voltage changes in the output of the GMR sensor or sensors 12. Accordingly, the digitizer 22 may capture the voltage changes in the output of the GMR sensor or sensors 12 and transmit a corresponding inspection signal 36 to the computer 16 through the communication pathway 28. The software 18 on the computer 16 may record the waveforms which correspond to the inspection signal 36. The software 18 may analyze the waveforms corresponding to the inspection signal 36 to indicate the presence and magnitude of the distortion 38 in the structure 32, as will be hereinafter further described.

As shown in FIG. 6, the GMR sensors 12 may be arranged in various orientations on the probe body 2 of the NDI probe 1. In some embodiments, the sensitive axes 66, 67 of the GMR sensors 12 may be disposed in a mixture of parallel and perpendicular orientations with respect to an inspection surface 32a of the structure 32. The sensitive axis 66 of at least one GMR sensor 12 may be disposed in perpendicular orientation with respect to the inspection surface 32a of the structure 32. The sensitive axis 67 of at least one GMR sensor 12 may be disposed in parallel orientation with respect to the inspection surface 32a of the structure 32.

Figure 7:
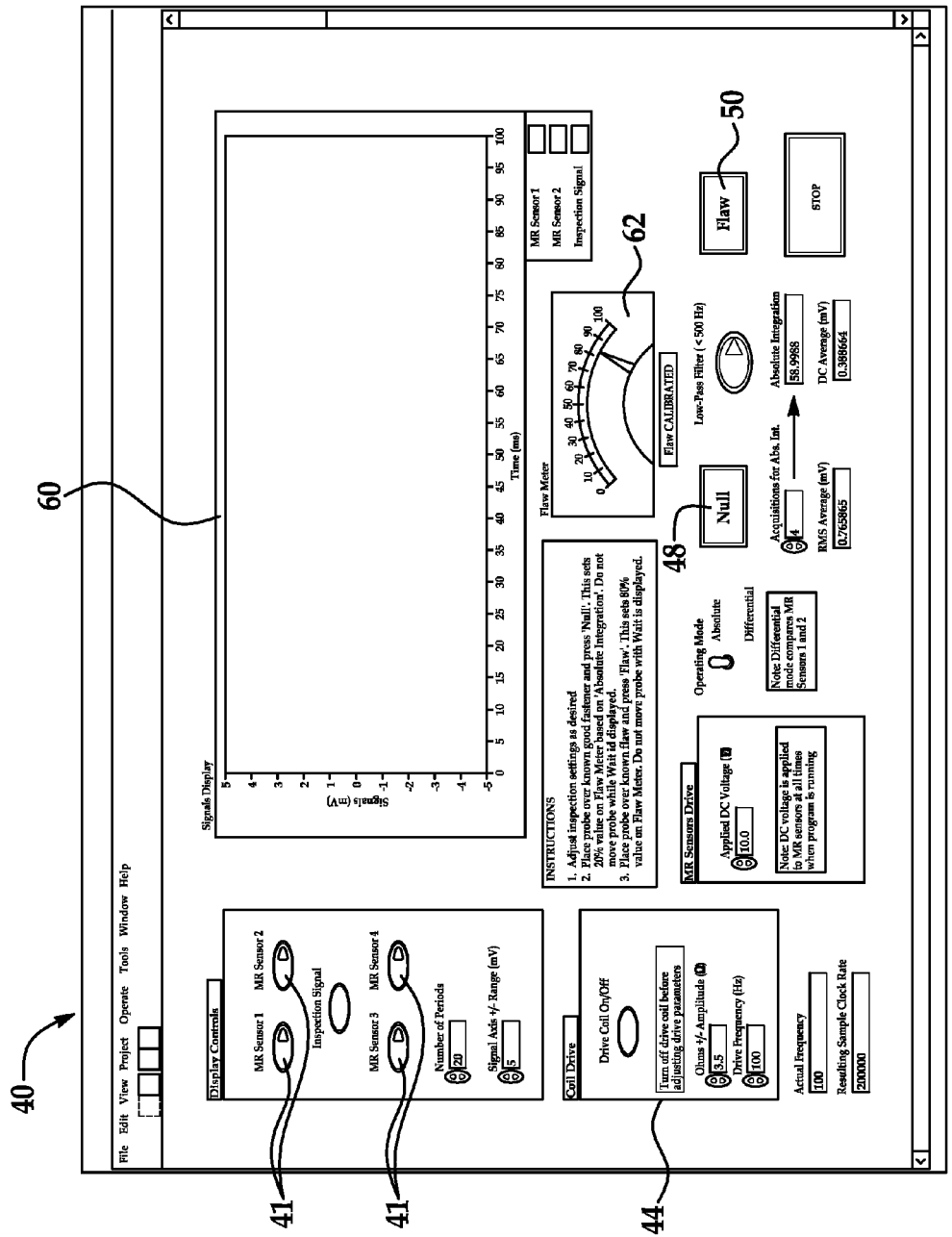
FIG. 7 is a software control panel and display which is suitable for implementation of an illustrative embodiment of the NDI probe.

Referring next to FIG. 7, an exemplary software control panel and display 40, hereinafter display 40, which is suitable for implementation of the NDI probe 1 is shown. The display 40 may include multiple sensor controls 41 which may be clicked to control operation of each of the GMR sensors 12 in the NDI probe 1. The display 40 may additionally include a coil drive control 44 which controls the eddy current excitation coil 8 of the NDI probe 1. The display 40 may further include a Null button 48 and a Flaw button 50, the purpose of which will be hereinafter described. A signal display 60 may be adapted to display the various waveforms of the inspection signal 36 (FIG. 5) which indicates the magnetic perturbation states of the GMR sensors 12. A flaw meter 62 may be adapted to indicate the magnitude of the distortion 38 (FIG. 6) which is detected in the structure 32 based on a percentage, as will be hereinafter further described.

Figure 8:
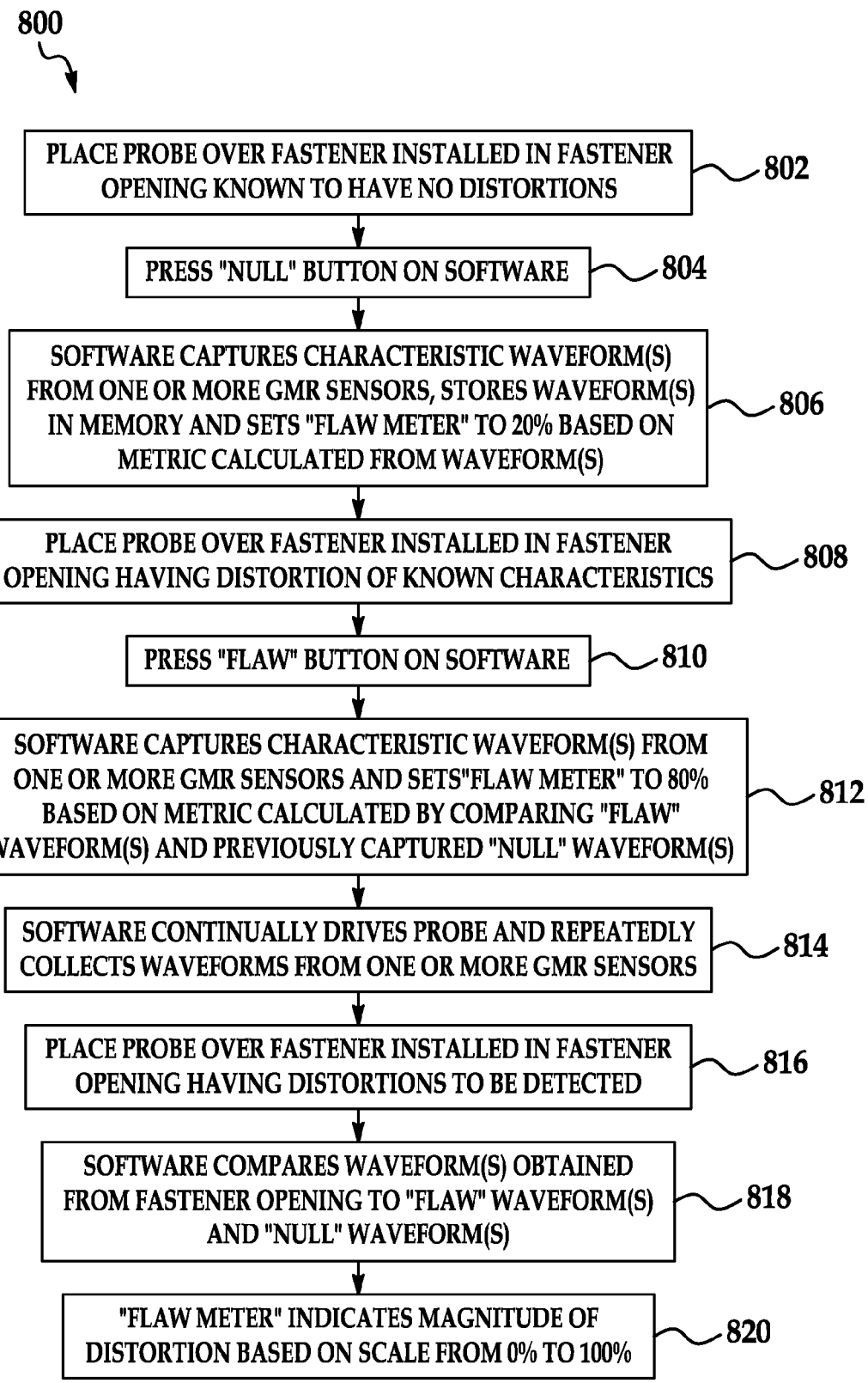
FIG. 8 is a flow diagram of an illustrative embodiment of an NDI method.

Referring next to FIGS. 6, 7 and 8, a flow diagram 800 of an illustrative embodiment of an NDI method in implementation of the NDI probe 1 (FIG. 6) is shown in FIG. 8. Calibration of the NDI probe 1 may be carried out as set forth in blocks 802-812. Accordingly, in block 802, the NDI probe 1 may initially be placed over a fastener 35 installed in a fastener opening 35a which is known to have no distortions 38. In block 804, the Null button 48 (FIG. 7) on the display 40 may be clicked. In block 806, the software 18 (FIG. 5) of the NDI system 15 may capture the characteristic "null" waveform(s) corresponding to the inspection signal 36 from one or more GMR sensors 1, store the waveform(s) in memory and set the flaw meter 62 (FIG. 7) to 20% based on a metric calculated from the waveform(s). In block 808, the NDI probe 1 may be placed over a fastener 35 installed in a fastener opening 35a having a distortion 38 of known characteristics. In block 810, the flaw button 50 (FIG. 7) on the display 40 may be clicked. In block 812, the software 18 may capture the characteristic "flaw" waveform(s) from one or more GMR sensors 12 and set the flaw meter 62 to 80% based on a metric calculated by comparing these "flaw" waveform(s) and the previously-captured "null" waveform(s).

In block 814, the software 18 may continually drive the NDI probe 1 and repeatedly collect waveforms from one or more GMR sensors 12 of the NDI probe 1. In block 816, the NDI probe 1 may be placed over the fastener 35 (FIG. 6) which is installed in a fastener opening 35a having distortions 38 to be detected. In block 818, the software 18 may compare the waveform(s) obtained from the fastener opening 35a to the "flaw" waveform(s) obtained in block 812 and the "null" waveform(s) obtained in block 806. In block 820, the flaw meter 62 (FIG. 7) on the display 40 may indicate the magnitude of the distortion 38 based on a scale of from 0% to 100%. A waveform of higher amplitude on the signal display 60 and reading on the flaw meter 62 above a threshold percentage value (such as 80%, for example and without limitation) may indicate that a distortion 38 emanates from the fastener opening 35a under inspection.

The software 18 may analyze the "flaw" waveforms and the "null" waveforms in various ways. Digital, low pass filtering may be applied to remove unwanted noise from the waveforms. After calibration by implementation of blocks 802-812, the "null" waveform may be subtracted from the waveform which is acquired during inspection of the structure 32 for display on the signal display 60. The waveform from one GMR sensor 12 may be subtracted from the waveform from another GMR sensor 12, revealing differences which may indicate a distortion 38 located beneath one or the other GMR sensor 12. All the waveforms from all the GMR sensors 12 may be added to each other to generate an aggregated waveform which may be used as the inspection signal 36 (FIG. 5). The aggregated calibration waveform may be subtracted from every successive acquisition.

It will be appreciated by those skilled in the art that the NDI probe 1 may be configured such as to not create DC magnetic fields in the vicinity of the GMR sensors 12. This expedient may conserve power and increase battery life of embodiments in which the NDI probe 1 is battery-operated. The NDI probe 1 may be capable of detecting smaller distortions 38 in a particular material stackup than can be achieved using conventional eddy current probes. Moreover, the NDI probe 1 may be capable of detecting a particular distortion 38 with a greater signal-to-noise ratio. The GMR sensors 12 of the NDI probe 1 are sensitive over a broader range of inspection frequencies than pickup coils and do not lose sensitivity at low frequencies as may be the case with pickup coils.

Figure 8A:
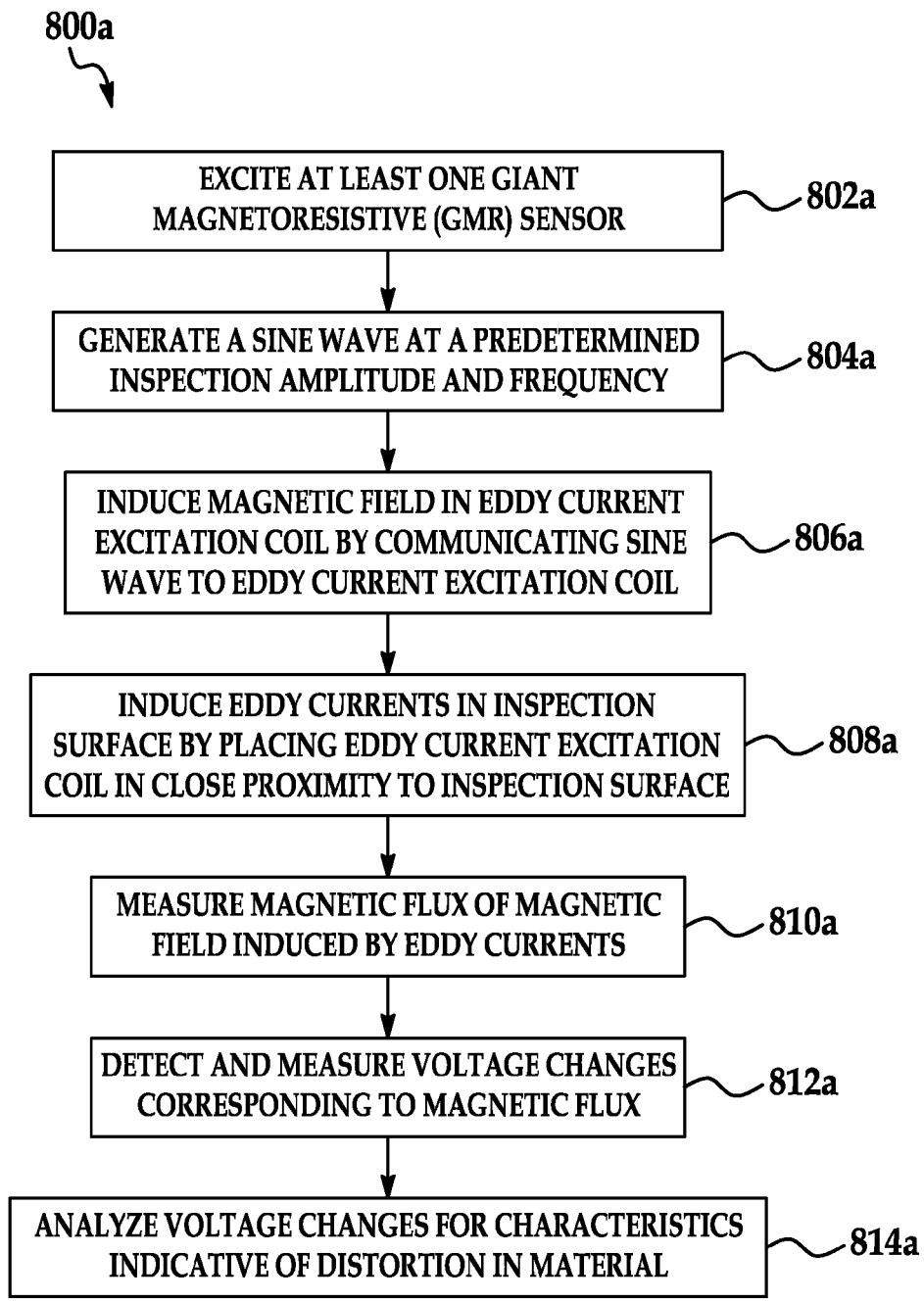
FIG. 8A is a flow diagram which summarizes an illustrative embodiment of an NDI method.

Referring next to FIG. 8A, a flow diagram which summarizes an illustrative embodiment of an NDI method is generally indicated by reference numeral 800a. In block 802a, at least one giant magnetoresistive (GMR) sensor is excited. In block 804a, a sine wave is generated at a predetermined inspection amplitude and frequency. In block 806a, a magnetic field is induced in an eddy current excitation coil by communicating the sine wave to the eddy current excitation coil. In block 808a, eddy currents are induced in an inspection surface by placing the eddy current excitation coil in close proximity with the inspection surface. In block 810a, a magnetic flux of the magnetic field induced by the eddy currents is measured. In some embodiments, measuring the magnetic flux may include measuring the magnetic flux along a plane parallel to the inspection surface. In some embodiments, measuring the magnetic flux may include measuring the magnetic flux along a plane perpendicular to the inspection surface. In some embodiments, measuring the magnetic flux may include measuring the magnetic flux along a plane parallel to the inspection surface and measuring the magnetic flux along a plane perpendicular to the inspection surface. In block 812a, voltage changes corresponding to the magnetic flux are detected and measured. In block 814a, the voltage changes are analyzed for characteristics indicative of a distortion in the material.

Figure 9:
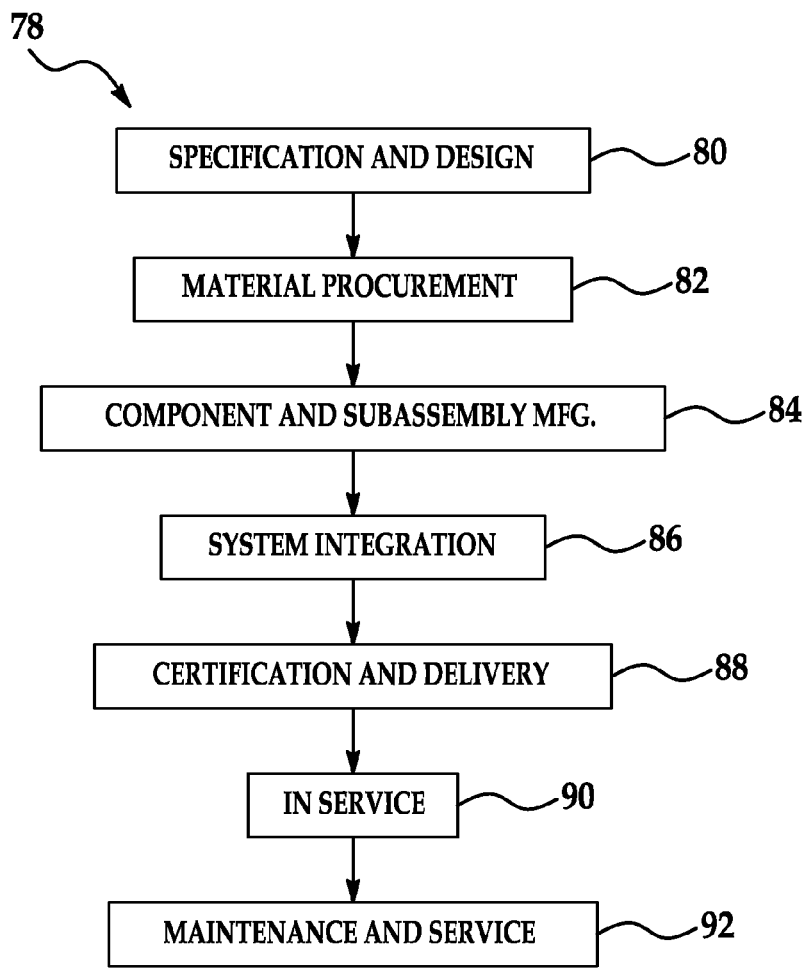
FIG. 9 is a flow diagram of an aircraft production and service methodology.
Figure 10:
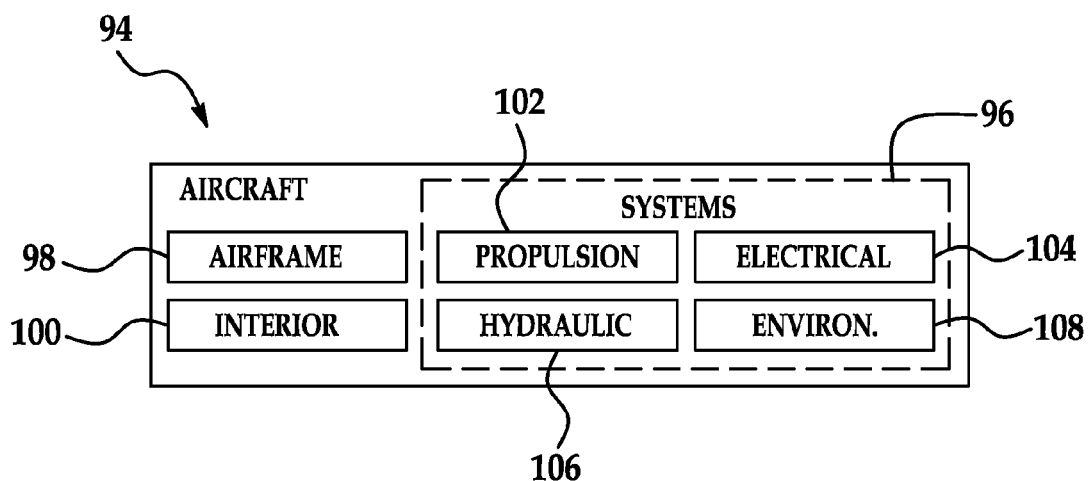
FIG. 10 is a block diagram of an aircraft.

Referring next to FIGS. 9 and 10, embodiments of the disclosure may be used in the context of an aircraft manufacturing and service method 78 as shown in FIG. 9 and an aircraft 94 as shown in FIG. 10. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 10, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A probe for detecting distortions in a material under test, comprising:
    a probe body;
    an inner shield in said probe body;
    an outer shield in said probe body surrounding said inner shield;
    an excitation coil between said outer shield and said inner shield, the excitation coil to generate eddy currents; and
    giant magnetoresistive (GMR) sensors disposed in magnetic field-communicating relationship with said excitation coil and in spaced-apart relationships with respect to each other around an axis of the excitation coil, the GMR sensors comprising:
        a first GMR sensor positioned such that a sensitive axis of the first GMR sensor has a parallel orientation with respect to an inspection surface of the material under test; and
        a second GMR sensor positioned such that a sensitive axis of the second GMR sensor has a perpendicular orientation with respect to the inspection surface of the material under test.

2. The probe of claim 1 wherein the first and second GMR sensors are inside said inner shield.

3. The probe of claim 2 wherein the GMR sensors are disposed in spaced-apart relationships with respect to each other inside said inner shield.

4. The probe of claim 1 wherein the first and second GMR sensors are outside said inner shield.

5. The probe of claim 1 wherein the first and second GMR sensors are generally aligned with said inner shield.

6. A probe for detecting distortions in a material under test, comprising:
    a probe body having a generally elongated, cylindrical probe body wall with a probe body interior;
    an inner shield in said probe body interior of said probe body;
    an outer shield in said probe body interior of said probe body and surrounding said inner shield;
    an excitation coil between said inner shield and said outer shield, the excitation coil to generate eddy currents;
    a plurality of giant magnetoresistive (GMR) sensors disposed in magnetic field-communicating relationship with said excitation coil; and
    a computer programmed to identify a first distortion in the material under test based on comparing a waveform collected by the GMR sensors from the material under test to a flaw waveform collected by the GMR sensors and comparing the waveform collected by the GMR sensors to a null waveform collected by the GMR sensors, the flaw waveform being representative of a second distortion in the material under test or in a second material, the second distortion having known characteristics, the null waveform being representative of a portion of the material under test having no known distortions or a portion of the second material having no known distortions.

7. The probe of claim 6 wherein said GMR sensors are positioned such that a sensitive axis of at least one of said GMR sensors has a parallel orientation with respect to an inspection surface of the material.

8. The probe of claim 6 wherein said GMR sensors are positioned such that a sensitive axis of at least one of said GMR sensors has a perpendicular orientation with respect to an inspection surface of the material.

9. The probe of claim 6 wherein at least one GMR sensor is positioned such that a sensitive axis of said GMR sensor has a parallel orientation with respect to an inspection surface of the material and at least one GMR sensor is positioned such that the sensitive axis of said GMR sensor has a perpendicular orientation with respect to the inspection surface of the material.

10. The probe of claim 6 wherein said GMR sensors are disposed in spaced-apart relationship with respect to each other around said excitation coil.

11. The probe of claim 6 wherein said GMR sensors are inside said inner shield.

12. The probe of claim 6 wherein said GMR sensors are outside said inner shield.

13. The probe of claim 6 wherein said GMR sensors are generally aligned with said inner shield.

14. A method for detecting distortions in a material under test, comprising:
    measuring a null waveform using at least one giant magnetoresistive (GMR) sensor from an unflawed portion of the material under test or a second material;
    measuring a flaw waveform using the at least one giant magnetoresistive (GMR) sensor from a portion of the material under test having a known flaw characteristic or a third material having the known flaw characteristic;
    exciting the at least one GMR sensor;
    generating a sine wave at a predetermined inspection amplitude and frequency;
    creating a magnetic field in an eddy current excitation coil by communicating said sine wave to said eddy current excitation coil;
    inducing eddy currents in the material under test by placing said eddy current excitation coil in close proximity with said material under test;
    measuring a magnetic flux of said magnetic field perturbed by said eddy currents;
    detecting and measuring voltage changes corresponding to said magnetic flux;
    and
    analyzing said voltage changes for characteristics indicative of a distortion in the material under test by comparing the voltage changes to at least one of the flaw waveform or the null waveform.

15. The method of claim 14 wherein said measuring the magnetic flux comprises measuring the magnetic flux along a plane parallel to an inspection surface of the material under test.

16. The method of claim 14 wherein said measuring the magnetic flux comprises measuring the magnetic flux along a plane perpendicular to an inspection surface of the material under test.

17. The method of claim 14 wherein said exciting at least one giant magnetoresistive (GMR) sensor comprises exciting a plurality of giant magnetoresistive sensors and said measuring the magnetic flux comprises measuring the magnetic flux along a plane parallel to an inspection surface of the material under test and measuring the magnetic flux along a plane perpendicular to said inspection surface.

18. The probe of claim 1, further comprising a computer programmed to identify a distortion in the material under test based on comparing a waveform collected by the GMR sensors from the material under test to a) a flaw waveform collected by the GMR sensors from a flawed portion of a second material or the material under test and to b) a null waveform collected by the GMR sensors from an unflawed portion of the second material, the material under test, or a third material.

19. The method of claim 14, further comprising:
  calculating a flaw metric by comparing the flaw waveform to the null waveform; and
  indicating the presence of a flaw in the material under test based on comparing the voltage changes to the flaw metric.

* * * * *